(12) United States Patent
Rush

(10) Patent No.: US 7,753,874 B2
(45) Date of Patent: Jul. 13, 2010

(54) FLUID DELIVERY DEVICE WITH AUTOCALIBRATION

(75) Inventor: Benjamin Rush, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

(21) Appl. No.: 12/345,603

(22) Filed: Dec. 29, 2008

(65) Prior Publication Data

US 2009/0177160 A1 Jul. 9, 2009

Related U.S. Application Data

(60) Division of application No. 11/105,711, filed on Apr. 13, 2005, now Pat. No. 7,727,181, which is a continuation-in-part of application No. 10/683,659, filed on Oct. 9, 2003, now Pat. No. 6,916,159.

(60) Provisional application No. 60/424,613, filed on Nov. 6, 2002, provisional application No. 60/417,464, filed on Oct. 9, 2002.

(51) Int. Cl.
*A61M 31/00* (2006.01)
(52) U.S. Cl. ...................................... 604/67
(58) Field of Classification Search .................. 604/65, 604/121, 122, 134, 151, 152, 67
See application file for complete search history.

(56) References Cited

U.S. PATENT DOCUMENTS

| | | | | |
|---|---|---|---|---|
| 2,915,579 A | * | 12/1959 | Mendelsohn | 429/254 |
| 3,606,592 A | * | 9/1971 | Madurski et al. | 417/413.1 |
| 3,750,687 A | * | 8/1973 | Williams | 137/1 |
| 3,843,455 A | * | 10/1974 | Bier | 35/284.1 |
| 3,923,060 A | * | 12/1975 | Ellinwood, Jr. | 604/891.1 |
| 3,930,493 A | * | 1/1976 | Williamson | 600/505 |
| 3,994,799 A | * | 11/1976 | Yao et al. | 604/5.04 |
| 4,018,547 A | * | 4/1977 | Rogen | 417/321 |
| 4,121,282 A | * | 10/1978 | Ohsawa | 363/21.08 |
| 4,146,029 A | * | 3/1979 | Ellinwood, Jr. | 604/891.1 |
| 4,193,397 A | * | 3/1980 | Tucker et al. | 604/502 |
| 4,268,173 A | * | 5/1981 | Barnard et al. | 356/445 |
| 4,439,197 A | * | 3/1984 | Honda et al. | 604/891.1 |
| 4,447,224 A | * | 5/1984 | DeCant et al. | 604/67 |
| 4,494,950 A | * | 1/1985 | Fischell | 604/66 |
| 4,529,401 A | * | 7/1985 | Leslie et al. | 604/131 |
| 4,531,235 A | * | 7/1985 | Brusen | 455/273 |
| 4,570,492 A | * | 2/1986 | Walsh | 73/861.05 |

(Continued)

FOREIGN PATENT DOCUMENTS

WO WO 2004032994 A2 * 4/2004

(Continued)

*Primary Examiner*—Nicholas D Lucchesi
*Assistant Examiner*—Aarti B Berdichevsky
(74) *Attorney, Agent, or Firm*—Jackson & Co., LLP

(57) ABSTRACT

A micro fluid delivery device is particularly useful in medical applications. The device may be worn or carried by the user and may deliver drugs or other medicaments to the user or patient. The device has a control system that accepts input from the user and controls all aspects of operation of the device. The control system measures the output of the pump and adjusts the output of the pump to achieve the desired dosage rate and size. This eliminates differences from pump to pump that result from inevitable variations in the manufacturing of such small scale affordable devices.

20 Claims, 6 Drawing Sheets

U.S. PATENT DOCUMENTS

| | | | |
|---|---|---|---|
| 4,686,624 A * | 8/1987 | Blum et al. | 346/20 |
| 4,850,959 A * | 7/1989 | Findl | 604/14 |
| 4,851,827 A * | 7/1989 | Nicholas | 345/93 |
| 4,866,396 A * | 9/1989 | Tamura | 329/352 |
| 4,976,590 A * | 12/1990 | Baldwin | 417/53 |
| 4,984,581 A * | 1/1991 | Stice | 600/585 |
| 5,004,532 A * | 4/1991 | Hale | 204/415 |
| 5,012,667 A * | 5/1991 | Kruse | 73/1.34 |
| 5,019,974 A * | 5/1991 | Beckers | 600/316 |
| 5,051,880 A * | 9/1991 | Harm et al. | 363/49 |
| 5,061,914 A * | 10/1991 | Busch et al. | 337/140 |
| 5,079,920 A * | 1/1992 | Whitehead et al. | 60/527 |
| 5,081,421 A * | 1/1992 | Miller et al. | 324/671 |
| 5,124,661 A * | 6/1992 | Zelin et al. | 324/601 |
| 5,205,819 A * | 4/1993 | Ross et al. | 604/67 |
| 5,207,666 A * | 5/1993 | Idriss et al. | 604/891.1 |
| 5,211,371 A * | 5/1993 | Coffee | 251/11 |
| 5,211,626 A * | 5/1993 | Frank et al. | 604/65 |
| 5,278,997 A * | 1/1994 | Martin | 455/127.1 |
| 5,324,599 A * | 6/1994 | Oyama et al. | 429/312 |
| 5,325,280 A * | 6/1994 | Tortola et al. | 362/234 |
| 5,366,292 A * | 11/1994 | Voss | 374/188 |
| 5,376,070 A * | 12/1994 | Purvis et al. | 604/31 |
| 5,391,250 A * | 2/1995 | Cheney et al. | 156/268 |
| 5,398,681 A * | 3/1995 | Kupershmidt | 600/316 |
| 5,404,585 A * | 4/1995 | Vimpari et al. | 455/115.1 |
| 5,406,301 A * | 4/1995 | Ravid | 345/34 |
| 5,448,992 A * | 9/1995 | Kupershmidt | 600/347 |
| 5,469,025 A * | 11/1995 | Kanemori et al. | 315/169.3 |
| 5,497,772 A * | 3/1996 | Schulman et al. | 600/347 |
| 5,507,288 A * | 4/1996 | Bocker et al. | 600/322 |
| 5,517,434 A * | 5/1996 | Hanson et al. | 361/679.41 |
| 5,559,528 A * | 9/1996 | Ravid et al. | 345/618 |
| 5,568,400 A * | 10/1996 | Stark et al. | 702/85 |
| 5,575,770 A * | 11/1996 | Melsky et al. | 604/288.04 |
| 5,604,404 A * | 2/1997 | Sahara | 315/8 |
| 5,622,413 A * | 4/1997 | Kim et al. | 303/119.2 |
| 5,622,482 A * | 4/1997 | Lee | 417/321 |
| 5,645,709 A * | 7/1997 | Birch et al. | 205/775 |
| 5,660,163 A * | 8/1997 | Schulman et al. | 600/345 |
| 5,661,643 A * | 8/1997 | Blakely et al. | 363/21.16 |
| 5,662,461 A * | 9/1997 | Ono | 417/418 |
| 5,671,301 A * | 9/1997 | Kupershmidt | 385/1 |
| 5,695,949 A * | 12/1997 | Galen et al. | 435/14 |
| 5,703,928 A * | 12/1997 | Galloway et al. | 379/21 |
| 5,748,872 A * | 5/1998 | Norman | 714/11 |
| 5,759,510 A * | 6/1998 | Pillai | 423/599 |
| 5,774,254 A * | 6/1998 | Berlin | 359/259 |
| 5,790,297 A * | 8/1998 | Berlin | 359/259 |
| 5,791,344 A * | 8/1998 | Schulman et al. | 600/347 |
| 5,815,303 A * | 9/1998 | Berlin | 359/196.1 |
| 5,822,715 A * | 10/1998 | Worthington et al. | 702/19 |
| 5,848,990 A * | 12/1998 | Cirelli et al. | 604/136 |
| 5,899,855 A * | 5/1999 | Brown | 600/301 |
| 5,913,833 A * | 6/1999 | Elstrom et al. | 600/573 |
| 5,923,512 A * | 7/1999 | Brownlow et al. | 361/78 |
| 6,027,459 A * | 2/2000 | Shain et al. | 600/573 |
| 6,027,496 A * | 2/2000 | Loomis et al. | 606/9 |
| 6,027,692 A * | 2/2000 | Galen et al. | 422/82.05 |
| 6,041,665 A * | 3/2000 | Hussain | 73/861.357 |
| 6,059,546 A * | 5/2000 | Brenan et al. | 417/534 |
| 6,063,039 A * | 5/2000 | Cunningham et al. | 600/573 |
| 6,066,243 A * | 5/2000 | Anderson et al. | 422/82.01 |
| 6,067,463 A * | 5/2000 | Jeng et al. | 600/336 |
| 6,071,249 A * | 6/2000 | Cunningham et al. | 600/578 |
| 6,071,251 A * | 6/2000 | Cunningham et al. | 600/584 |
| 6,073,031 A * | 6/2000 | Helstab et al. | 455/557 |
| 6,077,660 A * | 6/2000 | Wong et al. | 435/4 |
| 6,081,104 A * | 6/2000 | Kern | 323/268 |
| 6,085,871 A * | 7/2000 | Karamata | 184/75 |
| 6,093,156 A * | 7/2000 | Cunningham et al. | 600/573 |
| 6,129,823 A * | 10/2000 | Hughes et al. | 204/403.1 |
| 6,132,371 A * | 10/2000 | Dempsey et al. | 600/300 |
| 6,144,303 A * | 11/2000 | Federman | 340/573.4 |
| 6,144,922 A * | 11/2000 | Douglas et al. | 702/31 |
| 6,154,855 A * | 11/2000 | Norman | 714/10 |
| 6,155,992 A * | 12/2000 | Henning et al. | 600/583 |
| 6,157,442 A * | 12/2000 | Raskas | 356/39 |
| 6,160,449 A * | 12/2000 | Klomsdorf et al. | 330/149 |
| 6,162,202 A * | 12/2000 | Sicurelli et al. | 604/272 |
| 6,164,284 A * | 12/2000 | Schulman et al. | 128/899 |
| 6,173,160 B1 * | 1/2001 | Liimatainen | 455/67.11 |
| 6,175,752 B1 * | 1/2001 | Say et al. | 600/345 |
| 6,185,452 B1 * | 2/2001 | Schulman et al. | 604/20 |
| 6,206,841 B1 * | 3/2001 | Cunningham et al. | 600/584 |
| 6,208,894 B1 * | 3/2001 | Schulman et al. | 607/2 |
| 6,222,514 B1 * | 4/2001 | DeLuca | 345/84 |
| 6,242,961 B1 * | 6/2001 | Liu et al. | 327/307 |
| 6,245,060 B1 * | 6/2001 | Loomis et al. | 606/9 |
| 6,248,067 B1 * | 6/2001 | Causey et al. | 600/365 |
| 6,262,708 B1 * | 7/2001 | Chu | 345/667 |
| 6,278,425 B1 * | 8/2001 | DeLuca | 345/84 |
| 6,283,926 B1 * | 9/2001 | Cunningham et al. | 600/573 |
| 6,295,506 B1 * | 9/2001 | Heinonen et al. | 702/104 |
| 6,298,255 B1 * | 10/2001 | Cordero et al. | 600/372 |
| 6,306,104 B1 * | 10/2001 | Cunningham et al. | 600/573 |
| 6,312,888 B1 * | 11/2001 | Wong et al. | 435/4 |
| 6,315,721 B2 * | 11/2001 | Schulman et al. | 600/301 |
| 6,368,274 B1 * | 4/2002 | Van Antwerp et al. | 600/365 |
| 6,372,371 B1 * | 4/2002 | Iarochenko et al. | 429/27 |
| 6,375,344 B1 * | 4/2002 | Hanson et al. | 710/303 |
| 6,375,638 B2 * | 4/2002 | Nason et al. | 604/132 |
| 6,377,894 B1 * | 4/2002 | Deweese et al. | 702/22 |
| 6,381,496 B1 * | 4/2002 | Meadows et al. | 607/59 |
| 6,403,944 B1 * | 6/2002 | MacKenzie et al. | 250/214.1 |
| 6,408,402 B1 * | 6/2002 | Norman | 714/10 |
| 6,417,074 B2 * | 7/2002 | Kopley et al. | 438/448 |
| 6,419,642 B1 * | 7/2002 | Marchitto et al. | 600/573 |
| 6,425,829 B1 * | 7/2002 | Julien | 470/11 |
| 6,427,088 B1 * | 7/2002 | Bowman et al. | 607/60 |
| 6,432,585 B1 * | 8/2002 | Kawakami et al. | 429/233 |
| 6,437,379 B2 * | 8/2002 | Kopley et al. | 257/291 |
| 6,438,385 B1 * | 8/2002 | Heinonen et al. | 455/501 |
| 6,442,413 B1 * | 8/2002 | Silver | 600/345 |
| 6,466,807 B1 * | 10/2002 | Dobson et al. | 600/316 |
| 6,471,980 B2 * | 10/2002 | Sirhan et al. | 424/423 |
| 6,472,991 B1 * | 10/2002 | Schulman et al. | 340/995.1 |
| 6,492,180 B2 * | 12/2002 | Brown et al. | 436/77 |
| 6,506,168 B1 * | 1/2003 | Fathallah et al. | 600/578 |
| 6,514,460 B1 * | 2/2003 | Fendrock | 422/55 |
| 6,514,689 B2 * | 2/2003 | Han et al. | 435/4 |
| 6,522,530 B2 * | 2/2003 | Bang | 361/679.06 |
| 6,526,298 B1 * | 2/2003 | Khalil et al. | 600/310 |
| 6,535,753 B1 * | 3/2003 | Raskas | 600/310 |
| 6,540,891 B1 * | 4/2003 | Stewart et al. | 204/403.14 |
| 6,544,212 B2 * | 4/2003 | Galley et al. | 604/31 |
| 6,551,276 B1 * | 4/2003 | Mann et al. | 604/131 |
| 6,558,320 B1 * | 5/2003 | Causey et al. | 600/300 |
| 6,558,321 B1 * | 5/2003 | Burd et al. | 600/300 |
| 6,560,471 B1 * | 5/2003 | Heller et al. | 600/347 |
| 6,561,978 B1 * | 5/2003 | Conn et al. | 600/309 |
| 6,562,001 B2 * | 5/2003 | Lebel et al. | 604/65 |
| 6,564,105 B2 * | 5/2003 | Starkweather et al. | 607/60 |
| 6,564,807 B1 * | 5/2003 | Schulman et al. | 128/899 |
| 6,565,509 B1 * | 5/2003 | Say et al. | 600/365 |
| 6,565,738 B1 * | 5/2003 | Henning et al. | 205/777.5 |
| 6,569,157 B1 * | 5/2003 | Shain et al. | 606/12 |
| 6,571,128 B2 * | 5/2003 | Lebel et al. | 607/60 |
| 6,577,899 B2 * | 6/2003 | Lebel et al. | 607/60 |
| 6,582,393 B2 * | 6/2003 | Sage, Jr. | 604/65 |
| 6,585,644 B2 * | 7/2003 | Lebel et al. | 600/300 |
| 6,586,971 B1 * | 7/2003 | Naffziger et al. | 327/41 |
| 6,596,016 B1 * | 7/2003 | Vreman et al. | 607/88 |
| 6,600,997 B2 * | 7/2003 | Deweese et al. | 702/22 |

| Patent No. | Date | Inventor(s) | Class/Subclass |
|---|---|---|---|
| 6,602,469 B1 * | 8/2003 | Maus et al. | 422/68.1 |
| 6,615,061 B1 * | 9/2003 | Khalil et al. | 600/310 |
| 6,615,074 B2 * | 9/2003 | Mickle et al. | 600/509 |
| 6,641,533 B2 * | 11/2003 | Causey et al. | 600/300 |
| 6,648,821 B2 * | 11/2003 | Lebel et al. | 600/300 |
| 6,650,064 B2 * | 11/2003 | Guthrie et al. | 315/185 R |
| 6,659,948 B2 * | 12/2003 | Lebel et al. | 600/300 |
| 6,668,196 B1 * | 12/2003 | Villegas et al. | 607/60 |
| 6,669,663 B1 * | 12/2003 | Thompson | 604/67 |
| 6,669,669 B2 * | 12/2003 | Flaherty et al. | 604/132 |
| 6,679,841 B2 * | 1/2004 | Bojan et al. | 600/309 |
| 6,687,546 B2 * | 2/2004 | Lebel et al. | 607/60 |
| 6,692,457 B2 * | 2/2004 | Flaherty | 604/67 |
| 6,694,191 B2 * | 2/2004 | Starkweather et al. | 607/60 |
| 6,695,885 B2 * | 2/2004 | Schulman et al. | 623/25 |
| 6,702,857 B2 * | 3/2004 | Brauker et al. | 623/23.76 |
| 6,723,072 B2 * | 4/2004 | Flaherty et al. | 604/131 |
| 6,730,200 B1 * | 5/2004 | Stewart et al. | 204/403.11 |
| 6,731,976 B2 * | 5/2004 | Penn et al. | 600/544 |
| 6,733,446 B2 * | 5/2004 | Lebel et al. | 600/300 |
| 6,740,075 B2 * | 5/2004 | Lebel et al. | 604/891.1 |
| 6,741,877 B1 * | 5/2004 | Shults et al. | 600/345 |
| 6,752,787 B1 * | 6/2004 | Causey et al. | 604/131 |
| 6,758,810 B2 * | 7/2004 | Lebel et al. | 600/300 |
| 6,764,581 B1 * | 7/2004 | Forrow et al. | 204/403.14 |
| 6,768,425 B2 * | 7/2004 | Flaherty et al. | 340/870.07 |
| 6,799,861 B2 * | 10/2004 | Naghi et al. | 362/198 |
| 6,809,653 B1 * | 10/2004 | Mann et al. | 340/870.28 |
| 6,810,290 B2 * | 10/2004 | Lebel et al. | 607/60 |
| 6,811,533 B2 * | 11/2004 | Lebel et al. | 600/300 |
| 6,811,534 B2 * | 11/2004 | Bowman et al. | 600/300 |
| 6,813,519 B2 * | 11/2004 | Lebel et al. | 607/32 |
| 6,818,348 B1 * | 11/2004 | Venkatesan et al. | 429/217 |
| 6,832,114 B1 * | 12/2004 | Whitehurst et al. | 607/40 |
| 6,833,540 B2 * | 12/2004 | MacKenzie et al. | 250/214.1 |
| 6,835,553 B2 * | 12/2004 | Han et al. | 435/14 |
| 6,837,858 B2 * | 1/2005 | Cunningham et al. | 600/573 |
| 6,839,596 B2 * | 1/2005 | Nelson et al. | 607/59 |
| 6,840,912 B2 * | 1/2005 | Kloepfer et al. | 600/583 |
| 6,849,237 B2 * | 2/2005 | Housefield et al. | 422/82.01 |
| 6,859,831 B1 * | 2/2005 | Gelvin et al. | 709/224 |
| 6,862,465 B2 * | 3/2005 | Shults et al. | 600/347 |
| 6,873,268 B2 * | 3/2005 | Lebel et al. | 340/870.16 |
| 6,893,396 B2 * | 5/2005 | Schulze et al. | 600/300 |
| 6,895,265 B2 * | 5/2005 | Silver | 600/345 |
| 6,898,451 B2 * | 5/2005 | Wuori | 600/322 |
| 6,904,301 B2 * | 6/2005 | Raskas | 600/310 |
| 6,916,159 B2 * | 7/2005 | Rush et al. | 417/321 |
| 6,922,576 B2 * | 7/2005 | Raskas | 600/316 |
| 6,931,327 B2 * | 8/2005 | Goode et al. | 702/22 |
| 6,950,708 B2 * | 9/2005 | Bowman, IV et al. | 607/60 |
| 6,958,129 B2 * | 10/2005 | Galen et al. | 422/57 |
| 6,958,705 B2 * | 10/2005 | Lebel et al. | 340/870.07 |
| 6,974,437 B2 * | 12/2005 | Lebel et al. | 604/65 |
| 6,990,372 B2 * | 1/2006 | Perron et al. | 600/544 |
| 6,997,911 B2 * | 2/2006 | Klitmose | 604/232 |
| 7,003,340 B2 * | 2/2006 | Say et al. | 600/345 |
| 7,006,858 B2 * | 2/2006 | Silver et al. | 600/345 |
| 7,010,356 B2 * | 3/2006 | Jog et al. | 607/116 |
| 7,020,508 B2 * | 3/2006 | Stivoric et al. | 600/390 |
| 7,024,245 B2 * | 4/2006 | Lebel et al. | 607/32 |
| 7,024,249 B2 * | 4/2006 | Weisner et al. | 607/60 |
| 7,041,468 B2 * | 5/2006 | Drucker et al. | 435/14 |
| 7,043,287 B1 * | 5/2006 | Khalil et al. | 600/310 |
| 7,067,498 B2 * | 6/2006 | Wolf et al. | 514/54 |
| 7,070,591 B2 * | 7/2006 | Adams et al. | 604/891.1 |
| 7,072,738 B2 * | 7/2006 | Bonney et al. | 700/237 |
| 7,074,307 B2 * | 7/2006 | Simpson et al. | 204/403.04 |
| 7,077,328 B2 * | 7/2006 | Krishnaswamy et al. | 235/472.01 |
| 7,079,901 B1 * | 7/2006 | Loftin et al. | 607/60 |
| 7,081,195 B2 * | 7/2006 | Simpson et al. | 205/777.5 |
| 7,083,593 B2 * | 8/2006 | Stultz | 604/65 |
| 7,092,762 B1 * | 8/2006 | Loftin et al. | 607/60 |
| 7,097,983 B2 * | 8/2006 | Markovsky et al. | 435/7.1 |
| 7,098,803 B2 * | 8/2006 | Mann et al. | 340/870.07 |
| 7,108,778 B2 * | 9/2006 | Simpson et al. | 205/778 |
| 7,110,803 B2 * | 9/2006 | Shults et al. | 600/347 |
| 7,114,502 B2 * | 10/2006 | Schulman et al. | 128/899 |
| 7,123,206 B2 * | 10/2006 | Hess et al. | 343/788 |
| 7,133,710 B2 * | 11/2006 | Acosta et al. | 600/316 |
| 7,134,999 B2 * | 11/2006 | Brauker et al. | 600/300 |
| 7,136,689 B2 * | 11/2006 | Shults et al. | 600/347 |
| 7,136,704 B2 * | 11/2006 | Schulman | 607/22 |
| 7,149,581 B2 * | 12/2006 | Goedeke | 607/32 |
| 7,153,212 B1 * | 12/2006 | Karten et al. | 463/47 |
| 7,154,398 B2 * | 12/2006 | Chen et al. | 340/573.1 |
| 7,163,511 B2 * | 1/2007 | Conn et al. | 600/309 |
| 7,181,261 B2 * | 2/2007 | Silver et al. | 600/345 |
| 7,186,566 B2 * | 3/2007 | Qian | 436/524 |
| 7,186,791 B2 * | 3/2007 | Bruno et al. | 528/424 |
| 7,192,450 B2 * | 3/2007 | Brauker et al. | 623/23.76 |
| 7,198,603 B2 * | 4/2007 | Penner et al. | 600/486 |
| 7,202,734 B1 * | 4/2007 | Raab | 330/126 |
| 7,205,409 B2 * | 4/2007 | Pei et al. | 546/153 |
| 7,208,119 B1 * | 4/2007 | Kurtock et al. | 422/61 |
| 7,211,048 B1 * | 5/2007 | Najafi et | 600/508 |
| 7,225,535 B2 * | 6/2007 | Feldman et al. | 29/831 |
| 7,226,442 B2 * | 6/2007 | Sheppard et al. | 604/890.1 |
| 7,226,978 B2 * | 6/2007 | Tapsak et al. | 525/296 |
| 7,258,666 B2 * | 8/2007 | Brown | 600/300 |
| 7,266,400 B2 * | 9/2007 | Fine et al. | 600/316 |
| 7,276,029 B2 * | 10/2007 | Goode et al. | 600/365 |
| 7,299,080 B2 * | 11/2007 | Acosta et al. | 600/316 |
| 7,310,544 B2 * | 12/2007 | Brister et al. | 600/345 |
| 2001/0023095 A1 * | 9/2001 | Kopley et al. | 438/200 |
| 2001/0024864 A1 * | 9/2001 | Kopley et al. | 438/448 |
| 2002/0193679 A1 * | 12/2002 | Malave et al. | 600/407 |
| 2003/0023317 A1 * | 1/2003 | Brauker et al. | 623/23.76 |
| 2003/0032874 A1 * | 2/2003 | Rhodes et al. | 600/347 |
| 2003/0060765 A1 * | 3/2003 | Campbell et al. | 604/131 |
| 2003/0107487 A1 * | 6/2003 | Korman et al. | 340/573.1 |
| 2003/0198558 A1 * | 10/2003 | Nason et al. | 417/53 |
| 2003/0199825 A1 * | 10/2003 | Flaherty | 604/155 |
| 2003/0212346 A1 * | 11/2003 | Yuzhakov et al. | 600/584 |
| 2003/0217966 A1 * | 11/2003 | Tapsak et al. | 210/500.21 |
| 2003/0225360 A1 * | 12/2003 | Eppstein et al. | 604/19 |
| 2004/0011671 A1 * | 1/2004 | Shults et al. | 205/777.5 |
| 2004/0019321 A1 * | 1/2004 | Sage et al. | 604/65 |
| 2004/0045879 A1 * | 3/2004 | Shults et al. | 210/85 |
| 2004/0085215 A1 * | 5/2004 | Moberg et al. | 340/679 |
| 2004/0115067 A1 * | 6/2004 | Rush et al. | 417/322 |
| 2004/0122353 A1 * | 6/2004 | Shahmirian et al. | 604/65 |
| 2004/0132220 A1 * | 7/2004 | Fish | 436/525 |
| 2004/0133092 A1 * | 7/2004 | Kain | 600/377 |
| 2004/0152622 A1 * | 8/2004 | Keith et al. | 514/3 |
| 2004/0186362 A1 * | 9/2004 | Brauker et al. | 600/316 |
| 2004/0186365 A1 * | 9/2004 | Jin et al. | 600/365 |
| 2004/0193025 A1 * | 9/2004 | Steil et al. | 600/316 |
| 2004/0199059 A1 * | 10/2004 | Brauker et al. | 600/309 |
| 2004/0208780 A1 * | 10/2004 | Faries et al. | 422/3 |
| 2004/0263354 A1 * | 12/2004 | Mann et al. | 340/870.28 |
| 2005/0009126 A1 * | 1/2005 | Andrews et al. | 435/14 |
| 2005/0016276 A1 * | 1/2005 | Guan et al. | 73/579 |
| 2005/0031689 A1 * | 2/2005 | Shults et al. | 424/473 |
| 2005/0038680 A1 * | 2/2005 | McMahon | 705/3 |
| 2005/0043598 A1 * | 2/2005 | Goode et al. | 600/316 |
| 2005/0051580 A1 * | 3/2005 | Ramey | 222/390 |
| 2005/0053365 A1 * | 3/2005 | Adams et al. | 386/125 |
| 2005/0059926 A1 * | 3/2005 | Sage et al. | 604/65 |
| 2005/0065464 A1 * | 3/2005 | Talbot et al. | 604/66 |
| 2005/0090607 A1 * | 4/2005 | Tapsak et al. | 524/588 |
| 2005/0112169 A1 * | 5/2005 | Brauker et al. | 424/423 |
| 2005/0143635 A1 * | 6/2005 | Kamath et al. | 600/347 |
| 2005/0176136 A1 * | 8/2005 | Burd et al. | 435/287.2 |
| 2005/0182306 A1 * | 8/2005 | Sloan | 600/300 |

| | | | |
|---|---|---|---|
| 2005/0187720 A1* | 8/2005 | Goode et al. | 702/22 |
| 2005/0192557 A1* | 9/2005 | Brauker et al. | 604/503 |
| 2005/0235732 A1* | 10/2005 | Rush | 73/1.16 |
| 2005/0238503 A1* | 10/2005 | Rush et al. | 417/322 |
| 2005/0245795 A1* | 11/2005 | Goode et al. | 600/302 |
| 2005/0245799 A1* | 11/2005 | Brauker et al. | 600/347 |
| 2005/0249506 A1* | 11/2005 | Fuse | 398/183 |
| 2005/0249606 A1* | 11/2005 | Rush | 417/53 |
| 2006/0001551 A1* | 1/2006 | Kraft et al. | 340/870.16 |
| 2006/0015020 A1* | 1/2006 | Neale et al. | 600/309 |
| 2006/0016700 A1* | 1/2006 | Brister et al. | 205/777.5 |
| 2006/0019327 A1* | 1/2006 | Brister et al. | 435/25 |
| 2006/0020186 A1* | 1/2006 | Brister et al. | 600/345 |
| 2006/0020187 A1* | 1/2006 | Brister et al. | 600/345 |
| 2006/0020188 A1* | 1/2006 | Kamath et al. | 600/345 |
| 2006/0020189 A1* | 1/2006 | Brister et al. | 600/345 |
| 2006/0020190 A1* | 1/2006 | Kamath et al. | 600/345 |
| 2006/0020191 A1* | 1/2006 | Brister et al. | 600/345 |
| 2006/0020192 A1* | 1/2006 | Brister et al. | 600/345 |
| 2006/0036139 A1* | 2/2006 | Brister et al. | 600/345 |
| 2006/0036140 A1* | 2/2006 | Brister et al. | 600/345 |
| 2006/0036141 A1* | 2/2006 | Kamath et al. | 600/345 |
| 2006/0036142 A1* | 2/2006 | Brister et al. | 600/345 |
| 2006/0036143 A1* | 2/2006 | Brister et al. | 600/345 |
| 2006/0036144 A1* | 2/2006 | Brister et al. | 600/345 |
| 2006/0036145 A1* | 2/2006 | Brister et al. | 600/345 |
| 2006/0166629 A1* | 7/2006 | Reggiardo | 455/120 |
| 2006/0222566 A1* | 10/2006 | Brauker et al. | 422/68.1 |
| 2006/0224141 A1* | 10/2006 | Rush et al. | 604/503 |
| 2006/0247508 A1* | 11/2006 | Fennell | 600/345 |
| 2006/0273759 A1* | 12/2006 | Reggiardo | 320/110 |
| 2007/0078323 A1* | 4/2007 | Reggiardo et al. | 600/347 |
| 2007/0135697 A1* | 6/2007 | Reggiardo | 600/347 |
| 2007/0163880 A1* | 7/2007 | Woo et al. | 204/403.06 |
| 2007/0176867 A1* | 8/2007 | Reggiardo et al. | 345/87 |
| 2007/0203966 A1* | 8/2007 | Brauker et al. | 708/200 |
| 2007/0235331 A1* | 10/2007 | Simpson et al. | 204/403.01 |

FOREIGN PATENT DOCUMENTS

| | | |
|---|---|---|
| WO | WO 2006102412 A2 * | 9/2006 |
| WO | WO 2006110913 A2 * | 10/2006 |
| WO | WO 2006113521 A2 * | 10/2006 |

* cited by examiner

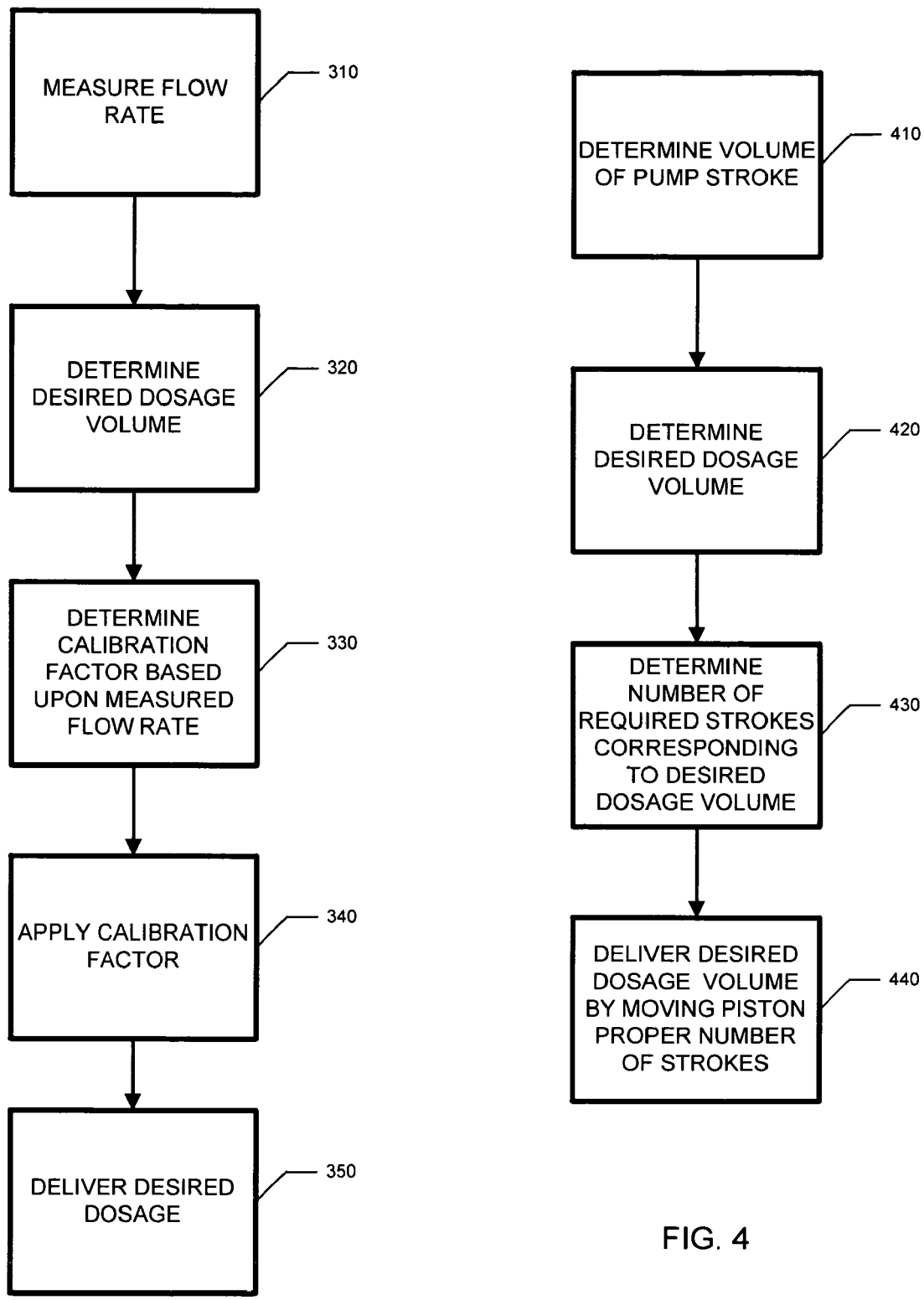

FLUID DELIVERY DEVICE WITH AUTOCALIBRATION

CROSS REFERENCE TO RELATED APPLICATIONS

The present application is a divisional of U.S. application Ser. No. 11/105,711 filed Apr. 13, 2005, now U.S. Pat. No. 7,727,181 which is a continuation-in-part of U.S. application Ser. No. 10/683,659 of Benjamin M. Rush et al., filed on Oct. 9, 2003, now U.S. Pat. No. 6,916,159 which is related to and claims priority based on U.S. Provisional Application No. 60/417,464, entitled "Disposable Pump for Drug Delivery System", filed on Oct. 9, 2002, and U.S. Provisional Application No. 60/424,613, entitled "Disposable Pump and Actuation Circuit for Drug Delivery System," filed on Nov. 6, 2002, each of which is hereby incorporated by this reference in its entirety. The parent application, U.S. application Ser. No. 10/683,659, was published as U.S. Patent Application Publication No. 2004/0115067 A1 and issued as U.S. Pat. No. 6,916,159 on Jul. 12, 2005. The present application is related to U.S. application Ser. No. 11/106,155 of Benjamin M. Rush et al., filed Apr. 13, 2005 entitled "Variable Volume, Shape Memory Actuated Insulin Dispensing Pump," and U.S. application Ser. No. 11/106,256 of Benjamin M. Rush, filed Apr. 13, 2005 entitled "Methods for Use in Assessing a Flow Condition of a Fluid," each of which is hereby incorporated herein, in its entirety, by this reference.

FIELD OF THE INVENTION

The present invention relates generally to fluid delivery devices such as pumps and relates more specifically to control and use of a small scale pump.

BACKGROUND OF THE INVENTION

Although the present invention may be used with many different types and sizes of pumps, the present invention is particularly useful with miniature or micro disposable pumps. One application for such a pump is in the delivery of insulin.

One type of miniature or micro pump utilizes a piston to push a volume of liquid defined by the volume (bore×stroke) of the piston and the volume of an accompanying diaphragm. A dose of the liquid, for example insulin, is said for purposes of discussion, to equal the volume of liquid expelled in one delivery stroke of the piston.

One characteristic of a miniature pump is that the piston diaphragm assembly requires extremely high manufacturing tolerances in order to generate a reproducible dose volume from one pump to the next. For example, with a typically sized miniature piston type pump the volume of the dose will vary by 0.5% per 1/10000 inch of variation in the stroke length. The stroke length is determined by the linear dimensions of three separate components, the piston, the cylinder, and the diaphragm, each of which has tolerances over 1/10000 inch. A coincidence of maximum variation in each of these components would result in a dose volume variation of ±15% from the nominal value. Additional tolerances associated with the diaphragm diameter and the piston head diameter further compound the problem.

Given that some applications of such a pump involve drug delivery, delivering a dose volume that is the same from pump to pump is non trivial. This is especially true in the case of disposable pumps, where a pump is regularly replaced with another pump of the same model. Regardless of the application of the pump, it is desirable to accommodate manufacturing tolerances and produce repeatable pumps with accurate dosage delivery.

SUMMARY OF INVENTION

The present invention provides a simple, inexpensive and reliable mechanism and method for determining the dose size produced by a given pump, which is then used to calibrate the pump and thereby normalize manufacturing variations in the volume of the pump. This results in more reliable and repeatable fluid delivery from one pump to the next of a given design.

Another aspect of the present invention comprises measuring the dose volume of a pump, preferably during the initial priming process, or alternatively anytime thereafter. This volume is then used to calibrate the timing of the dosing period. For example, if the actual measured volume of a particular pump is determined to be 15% larger than a basis value, such as the expected nominal value of the volume, then the timing of all subsequent delivery rates is reduced accordingly. The measurement can be made as part of the manufacturing process or can be made by the user as part of a pump initialization process. The measurement can also automatically be made by the pump at any time during operation of the pump. The calibration or adjustment of pump delivery is preferably made before usage of the pump by a user, but may be made any time during the life of the pump.

Another aspect involves a method of dispensing a liquid to a user with a portable dispensing device. The method comprises pumping the liquid, detecting arrival of the liquid at a first sensor, detecting arrival of the liquid at a second sensor, measuring the time elapsed from the arrival of the liquid at the first sensor to the arrival of the liquid at the second sensor, calculating the volumetric flow rate of the dispensing device, and adjusting the volumetric flow rate of the dispensing of the device.

Yet another aspect involves a method of administering a liquid including a drug to a user with a device worn or carried by a user. The method comprises providing a disposable component comprising a pump element, providing a durable component comprising a microprocessor, the disposable component configured to mate and operate with the durable component, initiating the flow of the liquid through a portion of the device with a known volume, the flow comprising a plurality of doses, determining the time necessary to pump the known volume, and determining the volume of a dose.

Additional aspects, advantages and features of the present invention are included in the following description of exemplary examples thereof, which description should be taken in conjunction with the accompanying figures, and wherein like (and similar) numerals are used to describe the same feature throughout the figures. All patents, patent applications, articles and other publications referenced herein are hereby incorporated herein by this reference in their entirety for all purposes.

BRIEF DESCRIPTION OF THE DRAWINGS

FIG. 3 is a flowchart depicting operation according to one embodiment of the present invention.

FIG. 4 is a flow chart of operation according to an embodiment of the present invention.

DETAILED DESCRIPTION OF THE PREFERRED EMBODIMENTS

Figure 1A:
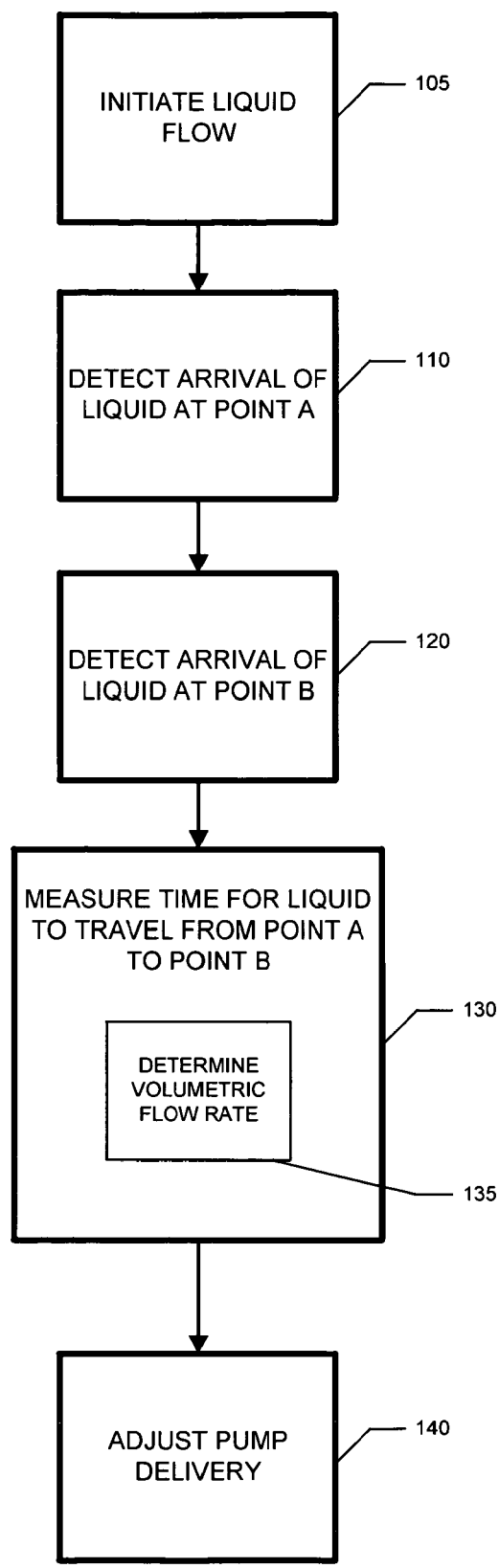
FIG. 1A is a flow chart of operation of an embodiment of the present invention.

It is important to eliminate the variations from one pump to the next (of the same design) that are a result of manufacturing limitations. The present invention can be used to minimize the effects of these variations and results in accurate delivery in any type of liquid pump.

As discussed in the background, there is one type of liquid pump with which the present invention is particularly advantageous, the miniature piston type pump. The piston diaphragm assembly of a miniature pump requires extremely high manufacturing tolerances in order to generate a reproducible dose volume from one pump to the next. Even with high precision manufacturing, a not insignificant variation from one pump to the next of a given design may be present. This is less than ideal, especially in applications of the pump involving drug delivery or other medicinal applications.

The present invention provides a simple, inexpensive and reliable mechanism and method for minimizing, or "zeroing out" the differences from pump to pump. One aspect involves a logic or processor controlled routine that may be thought of as an automatic calibration of the device. In a most general sense, this involves measuring the volume of a dosage produced by a given pump, comparing that dosage to a nominal dosage volume expected for that particular type of pump design, and then adjusting the pump output accordingly. This can also be accomplished by measuring the flow rate and then adjusting accordingly. Both volume and flow rate measurement comprise usage of one or more sensors that indicate the presence of liquid at a given point or points. Although there are many ways of adjusting the output of the pump, the preferred way of doing this is by calculating a ratio of a measured versus expected volume and calibrating the delivery based upon the ratio.

Although the present invention can be used with the delivery of any fluid in any environment, in the medical environment where the present invention is particularly suitable, the types of liquids that can be delivered include, but are not limited to: insulin, antibiotics, anesthetics, nutritional fluids, analgesics, hormones or related drugs, gene therapy drugs, anticoagulants, cardiovascular medications, HIV treatments, cancer treatments, etc. These can be delivered transcutaneously, through a type of patch on the skin, or the liquid may be evaporated and inhaled. The present invention is not limited to the delivery of these liquids or by the means of ingress into the patient's system, and these are only examples, not an exhaustive list.

Again, one application where the present invention may be particularly useful is in the delivery of insulin. Specifically, it may be useful in delivery of small quantities of insulin regularly with what is known as a miniature or micro pump. As the name implies, a miniature or micro pump delivers relatively small quantities. In the preferred embodiments described, which are tailored to insulin delivery, each actuation or dose of such a micro or miniature pump is on the order of approximately 0.5 to 5.0 microliters, with a potential total delivery of around 1000 microliters per day. Delivery volumes for other liquids (in the medical arena, that is) may be as high as around 5000 microliters or 5 cc's per day.

Figure 1B:
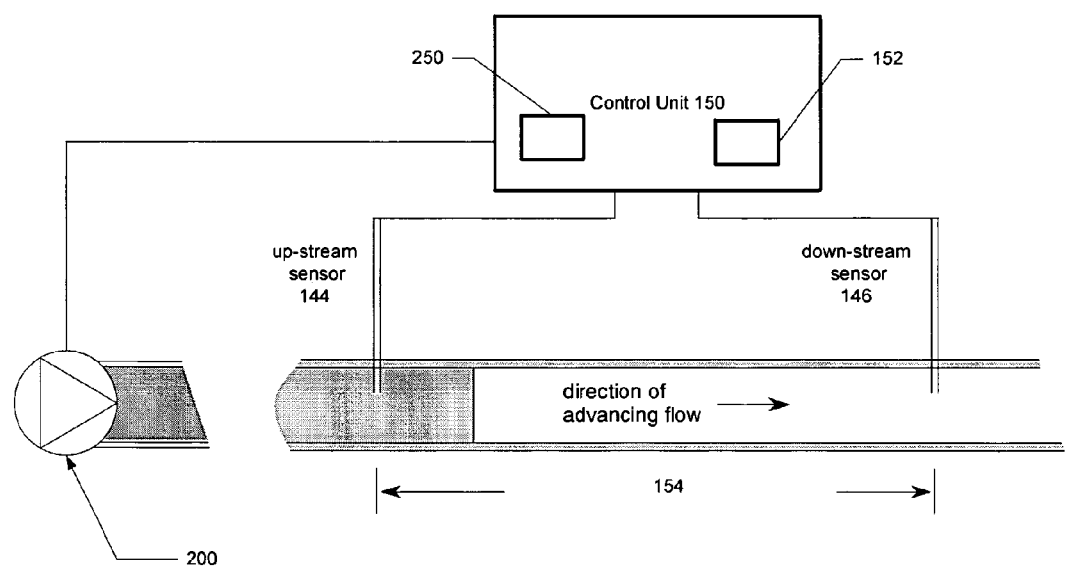
FIG. 1B is a diagram of an embodiment of the present invention referenced in FIG. 1A.

FIG. 1A is a flow chart describing operation according to an embodiment of the present invention seen in the schematic diagram of FIG. 1B. The process depicted in FIG. 1A can be performed at any time. It may also be done in conjunction with priming of the pump. In FIG. 1B there are two sensors, up-stream sensor 144, and down stream sensor 146, with a known volume between the two sensors. In this embodiment the known volume, or calibration region 154, has a cylindrical shape, but any geometric (regular or irregular) shape may be employed, so long as the volume is known or can be ascertained. The geometry of the calibration region should be such that it can be manufactured with sufficiently high reproducibility, and the volume of the calibration region is preferably much greater than the volume of an individual dose of insulin solution. This ensures good resolution and accuracy in the measurement. The sensors are connected to control unit 150, which is also connected to pump 200. Control unit 150 comprises drive circuitry 250 and logic unit 152, which is preferably in the form of a microprocessor. Each sensor comprises a pair of conductive electrodes, and when current passes between the electrodes of the pair, it indicates the presence of a liquid by the establishment of electrical continuity between the pair of electrodes. As long as the liquid has some measure of electrical conductivity, the presence of the liquid can be measured. As is appreciated in the art, the material of the electrodes may be tailored for the particular application. In the case of insulin, gold electrodes work well. As mentioned previously, pump 200 may be any type of liquid pump. In applications where cost is a driving factor, it is often preferable to utilize a pump that is driven by a shape memory actuator. This is particularly the case in the medical field, where devices are disposed of and replaced relatively frequently for various reasons.

The control unit 150 controls operation of the pump 200 and of the fluid delivery device generally, which may also comprise a user interface (not shown) for setting various operating parameters such as the delivery rate and for starting and stopping the device. The control unit also initiates and controls calibration of the device. For more information on the construction and operation of such a device, please refer to U.S. application Ser. No. 10/683,659 filed on Oct. 9, 2003, published as U.S. Patent Application Publication No. 2004/0115067 A1, and hereby incorporated by this reference in its entirety.

Returning to the flowchart of FIG. 1A, in step 105 the control unit initiates liquid flow. Then, in step 110, the control unit detects the arrival of the liquid at point A, which is a first point. This corresponds to up-stream sensor 144 in FIG. 1B. This can be done either when the liquid first advances or by placing an interruption in the flow stream before it reaches up-stream sensor 144. For instance, one way of interrupting the flow is to interject a gas bubble into the flow stream. In step 120, the control unit detects the arrival of the advancing liquid at point B, which corresponds to down-stream sensor 146 in FIG. 1B. In the case of a cylindrical calibration region 154 with a known diameter, the volume of the region is known if the distance between the two sensors is known.

In step 130, control unit 150 measures the time it takes for the liquid to travel from point A to point B. The volumetric flow rate is also calculated in step 135 based upon the time measured and the known volume between the points. This information is then used to adjust the delivery of the pump, as is seen in step 140. This process can take place at any time. It can be used initially to calibrate the pump, or during any time during operation of the device. Even if a discrete break is not inserted into the flow stream, the sensors may also indicate the flow rate of the device. The signal produced by the electrodes will increase as the rate of conduction of the liquid increases. Thus, given that the liquid is uniformly mixed, the signal will increase as the flow rate increases. For a given electrode/liquid combination, a profile of the output versus flow rate can be determined for given concentrations. The controller can then reference this data stored in memory to determine the flow rate. For more information on this, please refer to a co-pending U.S. application Ser. No. 11/106,256 of Benjamin M. Rush, entitled "Methods for Use in Assessing a Flow Condition of a Fluid," which is hereby incorporated by this reference in its entirety.

Figure 2B:
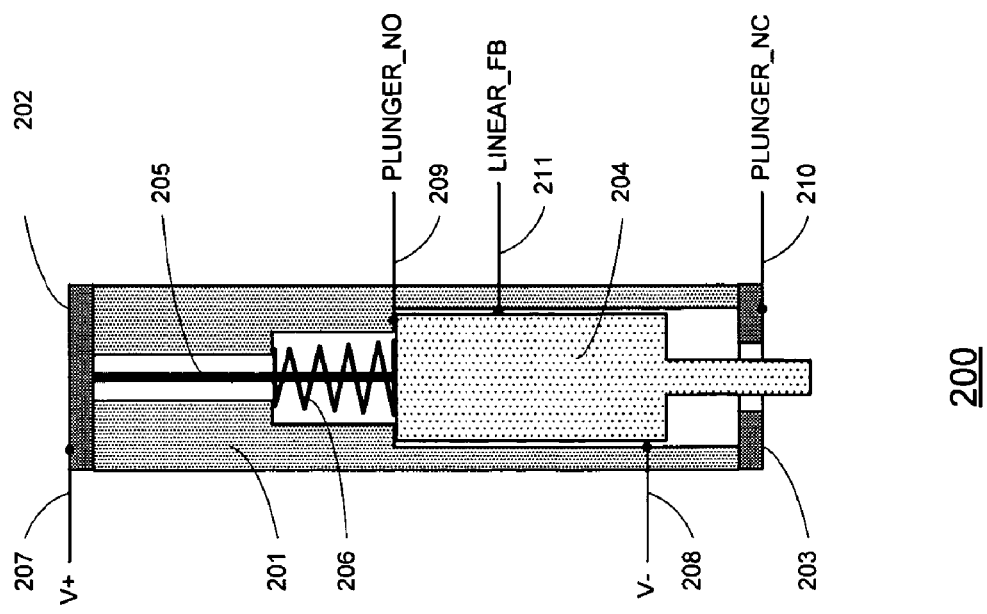
FIG. 2B illustrates pump 200, an embodiment of one type of pump that may be implemented with the present invention, shown in a second state.
Figure 2A:
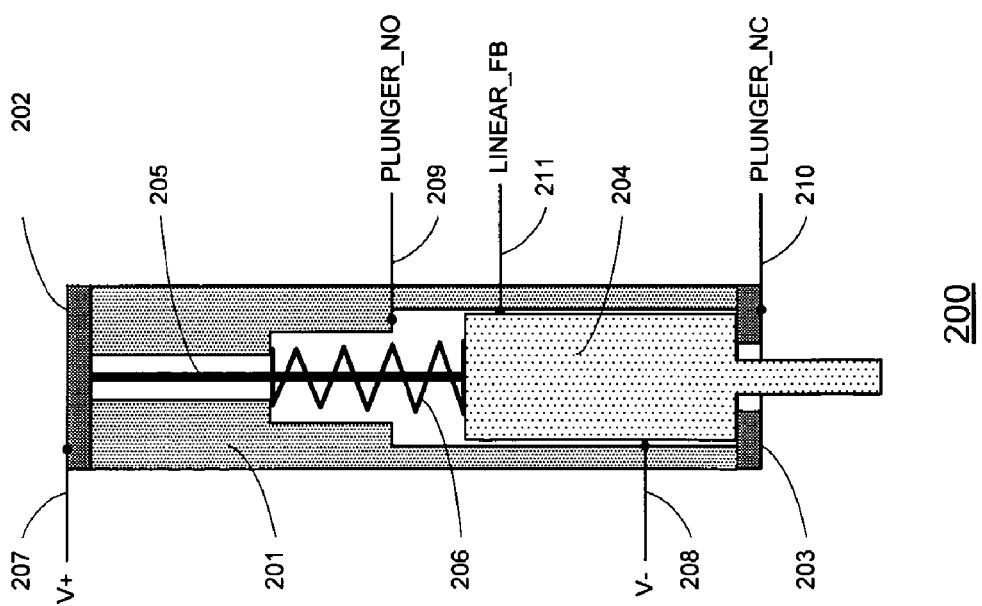
FIG. 2A illustrates pump 200, an embodiment of one type of pump that may be implemented with the present invention, shown in a first state.

FIGS. 2A and 2B illustrate pump 200, an embodiment of one type of pump particularly suited for use in the present invention. This pump is driven by a shape memory element 206 and employs feedback including that from switch 209, switch 210, and linear feedback system 211, all of which indicate the position of piston 204.

Pump 200 is shown in the inactive state in FIG. 2A, and the active state in FIG. 1B. Switch 209 indicates that the plunger or pump is in the open position, and switch 210 indicates it is in the closed position. The pump body comprises a case 201, a top cap 202, and a plunger cap 203. Within the pump is a plunger 204 that is normally (in the inactive state) held against the plunger cap 203 by a plunger bias spring 205. The plunger 204 is connected to shape memory element 206 which contracts when heated by a pulse or pulses of current flowing from the V+ 207 contact to the V− 208 contact through the shape memory element 206 (where the V− 208 contact may be the system ground reference). The power in each pulse is determined by the voltage applied to the shaped memory element through the contacts. It is worth noting that the case is made of an insulating material while the plunger is either made of a conductive material (e.g. metal) or is coated with an appropriately conductive material.

FIG. 2A depicts the pump in the inactive state where the shape memory element 206 is not contracted, and the plunger 204 is held against the plunger cap 203 by the plunger bias spring 205. This is the state to which the pump returns after each activation or pumping cycle.

FIG. 2B shows the pump in the active state where the shaped memory element 206 has contracted enough to pull the plunger 204 up against a stop built into the case 201.

Figure 2C:
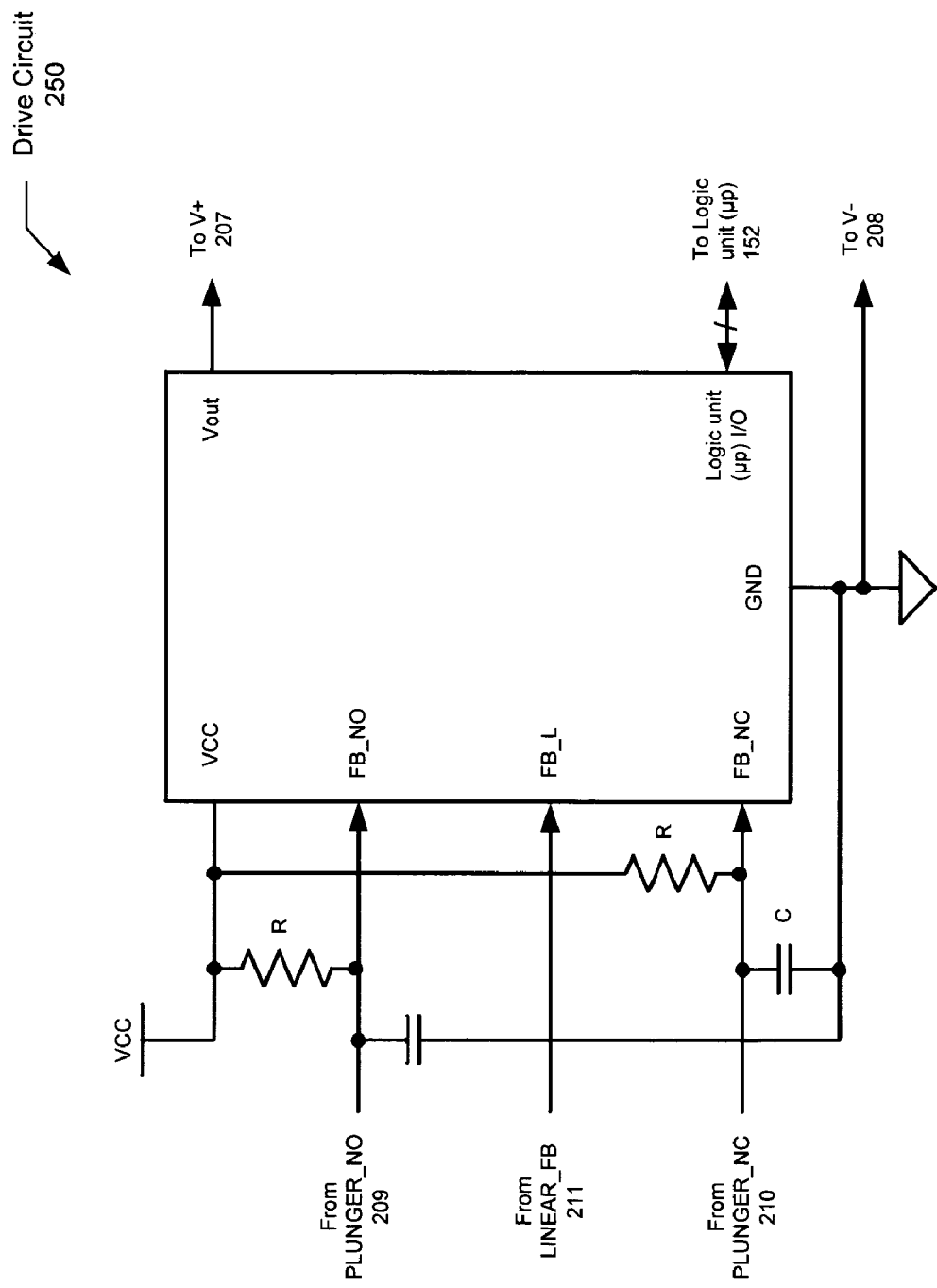
FIG. 2C is a diagram illustrating an example of a drive circuit for use with pump 200.

FIG. 2C illustrates drive circuit 250, an embodiment of a circuit that may be used with pump 200. Drive circuit 250 includes input and feedback to/from logic unit 152, which preferably comprises a microprocessor, as mentioned previously. For more information on this and other aspects of a shape memory actuated pump, please refer to co-pending U.S. application Ser. No. 11/106,155 of Benjamin M. Rush et al., entitled "Variable Volume, Shape Memory Actuated Insulin Dispensing Pump," which is hereby incorporated by this reference in its entirety.

FIG. 3 is a flowchart depicting operation according to one embodiment of the present invention. In step 310, the control unit measures the flow rate, as discussed earlier. Next in step 320, the system determines the desired dosage volume. This may be done automatically or may be entered by the user. In step 330, the system determines the calibration factor based upon the measured flow rate. The calibration factor preferably comprises a ratio of the expected volume of a dose versus the actual volume of a dose. In the case of the piston type pump earlier described, the calibration factor comprises a ratio of the nominal volume of the cylinder versus the actual volume of the cylinder. The nominal volume is either the value of the volume expected from the design specifications or the value expected based upon the nominal value of a large sample of production pieces. Once it has been determined, the calibration factor is applied in step 340 and will be applied to subsequent operation of the system, including when a desired dosage is delivered in step 350.

FIG. 4 is a flowchart depicting operation according to another embodiment of the present invention. In step 410, the volume delivered in one pump stroke is determined. In step 420, the system determines the desired dosage volume, which may be done automatically or entered by the user. Next in step 430 the system determines the number of required strokes corresponding to a desired dosage volume. Because of the linear feedback of the present invention, the system may deliver fractions of a stroke, and the number of strokes may include any number and fraction of strokes. Next, in step 440, the system delivers the desired dosage volume by moving the piston the proper number of strokes.

Figure 5:
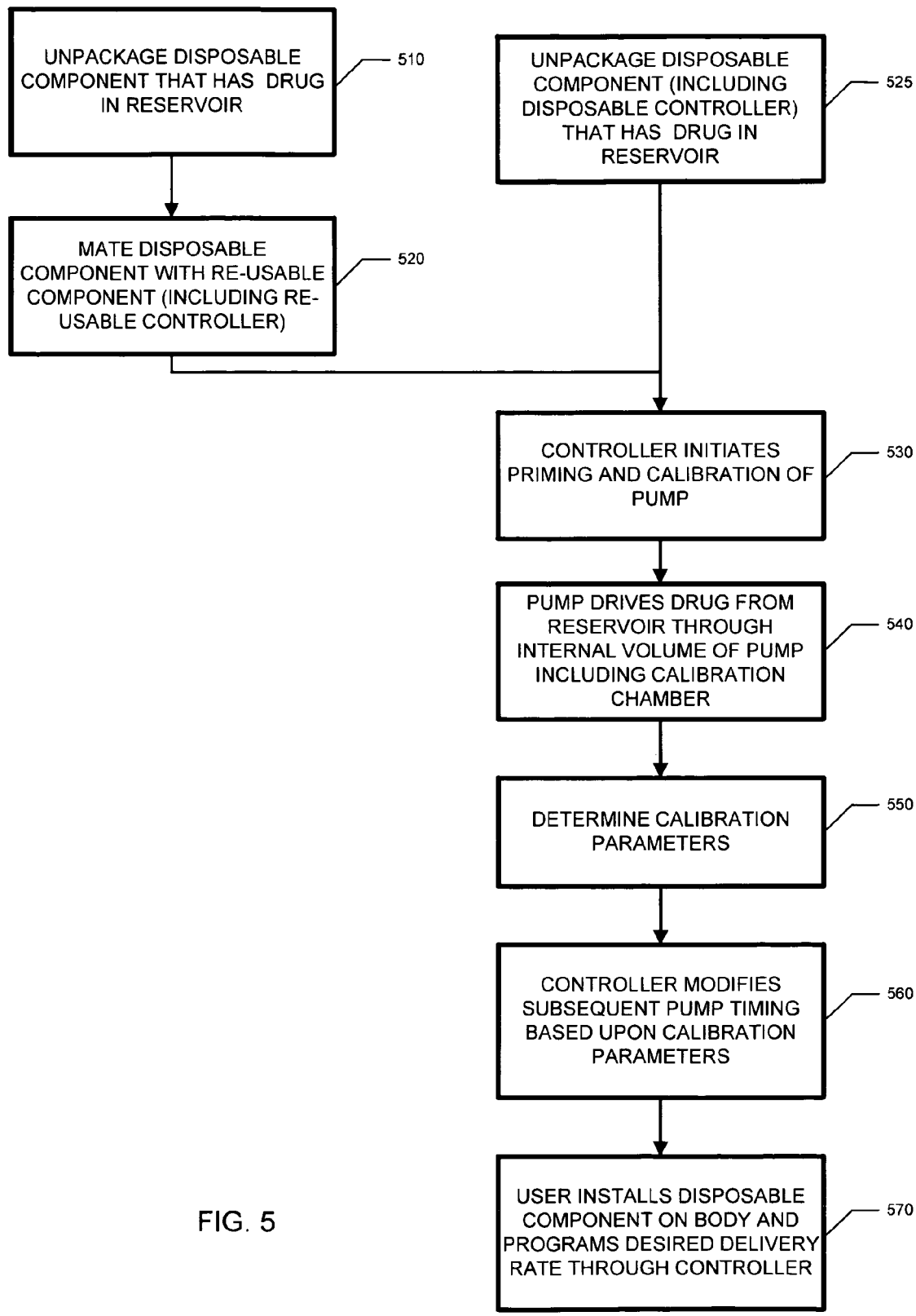
FIG. 5 is a flow chart of operation according to an embodiment of the present invention.

FIG. 5 is a flowchart depicting usage of two embodiments of the system. One embodiment comprises two units, a disposable unit and a re-usable unit, whereas the other embodiment incorporates all the components into one disposable unit. Some or all of the parts of the system shown in FIG. 1B may be reusable, but in the case where there exists a reusable component, it comprises control unit 150. The term disposable refers to the ordinary meaning of the word, and is involves intended usage on the order of days to months. The term reusable also refers to the ordinary meaning and describes a durable component with an intended usage on the order of months to years.

In step 510, the user unpackages the disposable component that has a selected liquid or drug in a reservoir. Next, in step 520, the user mates the disposable component with the re-usable component.

Alternatively, the user simply unpackages the system (pre-loaded with the liquid in the reservoir), which is entirely disposable, in step 525.

Thereafter, the controller initiates priming and calibration of the pump in step 530. In step 540, the pump then drives the liquid from the reservoir through the internal volume of the pump, including through calibration region 154. Next in step 550, calibration parameters, such as the calibration factor are determined. Thereafter, in step 560, the controller modifies the subsequent pump timing based upon the calibration parameters. For instance, if the calibration parameters indicate the measured volume of a particular pump is less than the expected nominal volume of production units, the dosage frequency will be increased. In step 570, the user installs the disposable component (including the controller in one embodiment) and programs the desired delivery rate through the controller user interface. Step 560 may occur before or after step 570, and there is no particular order of the steps unless explicitly stated.

EXPERIMENTAL RESULTS

An embodiment of the present invention was tested in three trials. The dose volume was determined with the embodiment and compared to a gravimetric determination of the dose volume. The results confirm the accuracy of measurements made with the embodiment. The results of three measurements are shown below.

A functional model of the calibration device of the present invention was constructed of a length of tubing with an outer diameter of 0.125 inches and an inner diameter of 0.0625 inches. The sensors were pairs of copper wire and electrical continuity between the two wires of a given pair was measured as an indication of wetting by insulin. A small voltage was applied between each of the sensor electrode pairs. At the point at which the leading edge of the advancing insulin contacted either of the sensor electrode pairs, a circuit was completed resulting in the flow of current through the circuit. This current flow was detected by monitoring the voltage across a current sensing resistor placed in each sensor circuit. The time required for the leading edge of the advancing insulin to traverse the distance between the two sensors was monitored with a timing device.

As can be seen below, three trial measurements were consistent to within 1% and agreed with the two gravimetric measurements to within 1%. The two gravimetric measurements agreed to within 2%. The measurement made with the functional model is approximately the average of the two gravimetric measurements. This confirms the accuracy of the present invention.

| Test Calibration Region | |
|---|---|
| ID: | 1.588 mm (0.0625") |
| Cross sectional area: | 1.979 mm$^2$ |
| Electrode spacing: | 76.20 mm (3.00") |
| Volume: | 150.80 mm$^3$ |
| Trial 1 | |
| Dose period: | 14.92 seconds |
| Time to traverse electrodes: | 1003 seconds |
| Doses to traverse electrodes: | 67 (rounded to nearest whole) |
| Dose volume: | 2.251 mm$^3$ |
| Measured dose volume (gravimetric): | 188.47 mg/83 doses = 2.271 mg/dose |
| Ratio: | 0.99 |
| Trial 2 | |
| Dose period: | 14.92 seconds |
| Time to traverse electrodes: | 996 seconds |
| Doses to traverse electrodes: | 67 (rounded to the nearest whole) |
| Dose volume: | 2.251 mm$^3$ |
| Measured dose volume (gravimetric): | N/A |
| Ratio: | N/A |
| Trial 3 | |
| Dose period: | 14.92 seconds |
| Time to traverse electrodes: | 995 seconds |
| Doses to traverse electrodes: | 67 (rounded to nearest whole) |
| Dose volume: | 2.251 mm$^3$ |
| Measured dose volume (gravimetric): | 184.64 mg/83 doses = 2.225 mg/dose |
| Ratio: | 0.99 |

Although the various aspects of the present invention have been described with respect to exemplary embodiments thereof, it will be understood that the present invention is entitled to protection within the full scope of the appended claims.

It is claimed:

1. A method of delivering a dosage of liquid with a piston actuated pump, the piston having a stroke length, the method comprising:
   measuring a flow rate of the pump;
   determining a flow characteristic of the liquid substantially simultaneously with measuring the flow rate of the pump, wherein the flow characteristic of the liquid corresponds to a rate of an electrochemical reaction of a component of the liquid;
   determining a desired dosage;
   determining a number of strokes corresponding to the desired dosage, wherein the determined number of strokes is based, at least in part, on the measured flow rate and the determined flow characteristic of the liquid; and
   delivering the desired dosage by moving the piston the corresponding number of strokes.

2. The method of claim 1, wherein measuring the flow rate comprises detecting a constituent in a liquid with one or more electrodes.

3. The method of claim 1, wherein the liquid is insulin.

4. The method of claim 1, wherein determining a desired dosage includes automatically determining a desired dosage.

5. The method of claim 1, wherein determining a desired dosage includes receiving user input corresponding to the desired dosage.

6. The method of claim 1, wherein moving the piston comprises altering the shape of a shape memory actuator by applying a potential to the actuator.

7. The method of claim 6, further comprising altering the potential based upon feedback from a signal from one or more sensors indicative of the position of the piston.

8. The method of claim 1, wherein measuring the flow rate comprises:
   actuating the pump;
   noting when liquid moved by the pump passes a first sensor; and
   noting when liquid moved by the pump passes a second sensor.

9. The method of claim 8, wherein a volume of a portion of the pump between the first and second sensor is known and measuring the flow rate further comprises calculating the number of times the piston is actuated in order to produce the known volume.

10. A method of delivering a liquid, the method comprising:
    measuring a flow rate of the liquid by determining when the liquid passes a first sensor having a plurality of electrodes and second sensor having a plurality of electrodes;
    determining a flow characteristic of the liquid substantially simultaneously with measuring the flow rate of the liquid;
    receiving a desired dosage amount;
    determining a number of strokes of a piston required to give the desired amount, wherein the determined number of strokes is based, at least in part, on the measured flow rate and the determined flow characteristic; and
    moving the piston the determined number of strokes to deliver the liquid.

11. The method of claim 10, wherein the liquid is insulin.

12. The method of claim 10, wherein the flow characteristic of the liquid corresponds to a voltage of a reaction rate associated with a component of the liquid.

13. The method of claim 10, wherein moving the piston comprises altering the shape of a shape memory actuator by applying a potential to the actuator.

14. The method of claim 10, wherein the plurality of electrodes of the first sensor and the plurality of electrodes of the second sensor are configured to detect an interruption in a flow stream of the liquid.

15. A device for delivering a dosage of liquid, the device comprising:
    a piston actuated pump, wherein the piston has a stroke length;
    a first sensor and a second sensor for measuring a flow rate of the liquid;

a third sensor for determining a flow characteristic of the liquid;

a shape memory element configured to move the piston from a first point in a stroke length to a second point in a stroke length; and a processor configured to:
  determine a desired dosage;
  determine a number of strokes corresponding to the desired dosage, wherein the determined number of strokes is based, at least in part on the measured flow rate and the determined flow characteristic; and
  actuate the shape memory element to move the piston the determined number of strokes.

16. The device of claim 15, further comprising a linear feedback switch, wherein the linear feedback switch monitors the piston when the piston is actuated for the determined number of strokes.

17. The device of claim 15, wherein each of the first sensor and the second sensor have a plurality of electrodes.

18. The device of claim 17, wherein the plurality of electrodes of the first sensor and the second sensor are configured to detect an interruption in a dosage of liquid.

19. The device of claim 15, wherein the flow characteristic of the liquid corresponds to a voltage of a reaction rate associated with a component of the liquid.

20. The device of claim 19, wherein actuating the shape memory element comprises modifying the temperature of the shape memory element.

* * * * *